United States Patent [19]

Kaswan

[11] Patent Number: 5,411,952
[45] Date of Patent: * May 2, 1995

[54] OCULAR CYCLOSPORINE COMPOSITION

[75] Inventor: Renee Kaswan, Athens, Ga.

[73] Assignee: University of Georgia Research Foundation, Inc., Atlanta, Ga.

[*] Notice: The portion of the term of this patent subsequent to Jun. 13, 2006 has been disclaimed.

[21] Appl. No.: 474,683

[22] Filed: Feb. 6, 1990

Related U.S. Application Data

[63] Continuation of Ser. No. 187,823, Apr. 29, 1988, abandoned, which is a continuation-in-part of Ser. No. 092,466, Sep. 3, 1987, Pat. No. 4,839,342, and Ser. No. 117,218, Nov. 4, 1987, abandoned.

[51] Int. Cl.$^6$ ............................................. A61K 37/02
[52] U.S. Cl. ............................................. 514/11; 514/9; 514/912; 514/914; 530/317; 530/321; 424/427; 424/485
[58] Field of Search ............... 514/11, 9, 912, 914; 530/317, 321; 424/427, 485

[56] References Cited

U.S. PATENT DOCUMENTS

| | | | |
|---|---|---|---|
| 4,108,985 | 8/1978 | Ruegger et al. | 514/11 |
| 4,117,118 | 9/1978 | Harri et al. | 514/11 |
| 4,210,581 | 7/1980 | Ruegger et al. | 530/321 |
| 4,215,199 | 7/1980 | Harri et al. | 435/71 |
| 4,220,641 | 9/1980 | Traber et al. | 514/11 |
| 4,288,431 | 9/1981 | Traber et al. | 514/11 |
| 4,289,851 | 9/1981 | Traber et al. | 514/11 |
| 4,384,996 | 5/1983 | Bollinger et al. | 530/321 |
| 4,388,307 | 6/1983 | Cavanak | 514/11 |
| 4,396,542 | 8/1983 | Wenger | 530/321 |
| 4,554,351 | 11/1985 | Wenger | 544/177 |
| 4,639,434 | 11/1987 | Wenger et al. | 530/321 |
| 4,649,047 | 3/1987 | Kaswan | 424/78 |
| 4,681,754 | 7/1987 | Siegl | 424/10 |
| 4,703,033 | 10/1987 | Seebach | 514/11 |
| 4,745,100 | 5/1988 | Gilbard et al. | 514/912 |
| 4,923,699 | 5/1990 | Kaufman | 424/427 |
| 4,963,367 | 10/1990 | Ecanow | 424/485 |

FOREIGN PATENT DOCUMENTS

| | | | |
|---|---|---|---|
| 0019197 | 8/1970 | Australia | 424/78 |
| 61-249918 | 11/1986 | Japan . | |
| 8301252 | 4/1983 | WIPO | 424/177 |
| 8404680 | 12/1984 | WIPO | 514/912 |

OTHER PUBLICATIONS

Hunter et al, Clin. Exp. Immunol., vol. 45, pp. 173–177, (1981).
Abelson, et al. *Amer. J. Ophthal.* 95, 500–505 (1983).
Abiose, et al. *Annals of Ophthal.* 15(8), 744–747, (1983).
Allansmith *Clinical Ophthalmology,* Chapter 9, vol. 4 pp 1–8 (Harper & Row 1986).
BenEzra, et al., *Amer. J. Ophthal.* 101, 278–282 (1986).
Grayson, *Diseases of the Cornea* pp. 334–367 (C. V. Mosby Co. 1983).
F. Hoffman and M. Wiederholt, *Klin. Mbl. Augenheilk.* 198, 92–95 (1985). (with translation).
Lemp, *Clinical Ophthalmology* vol. 4, pp. 1–10, Duane and Jaeger, editors (Harper & Row 1986).
Williams, et al., *Transplantation* 39(3), 242–244 (1985).
Williams, et al., *British J. Ophthal* 71, 239–242 (1987).

(List continued on next page.)

*Primary Examiner*—Jill Warden
*Assistant Examiner*—T. D. Wessendorf
*Attorney, Agent, or Firm*—Kilpatrick & Cody

[57] ABSTRACT

Cyclosporine compositions for topical ophthalmic use for treatment of immune disorders, to enhance or restore tear production, and to enhance or effect normal healing of the surface of the eye, containing cyclosporine dissolved in corn oil. The composition may further include antioxidants, lubricants, antibiotics, antifungals, antivirals, pilocarpine, vasoconstrictors, surfactants, wetting agents, anti-inflammatory agents (i.e. corticosteroids), preservatives, mucolytic agents (i.e. bromhexine, acetylcysteine), as well as other compounds.

The preferred composition is 2% cyclosporine, 1 mole % alpha tocopherol and 0.005% methyl paraben in corn oil.

12 Claims, 2 Drawing Sheets

OTHER PUBLICATIONS

Kossendrup, et al., *Cornea* 4, 177–181 (1985).
Foets, et al., *Brit. J. Ophthal.* 69, 600–603 (1983).
Nussenblat, et al., *Arch Ophthal.* 103, 1559–1562 (1985).
Hoffmann, et al., *Cornea* 4, 3–7 (1985–1986).
Grisolano, et al., *Ophthal. Surg.* 17, 155–156 (1986).
Oh, et al., *Invest. Ophthal. Vis. Sci.* 26(4), 494–500 (1985).
Boisjoly, et al., *Arch. Ophthalmol.* 102. 1804–1807 (1984).
Hunter, et al., *Clin. Exp. Immunol.* 45, 173–177 (1981).
Singh, et al., *Cornea* 3, 272–277 (1985).
Klin., Mbl. Augenheik, 187(1985), Hoffmann, pp. 92–95.
Am. Journal of Ophthalmology 101, pp. 278–282, 1986, Ben Erza et al.

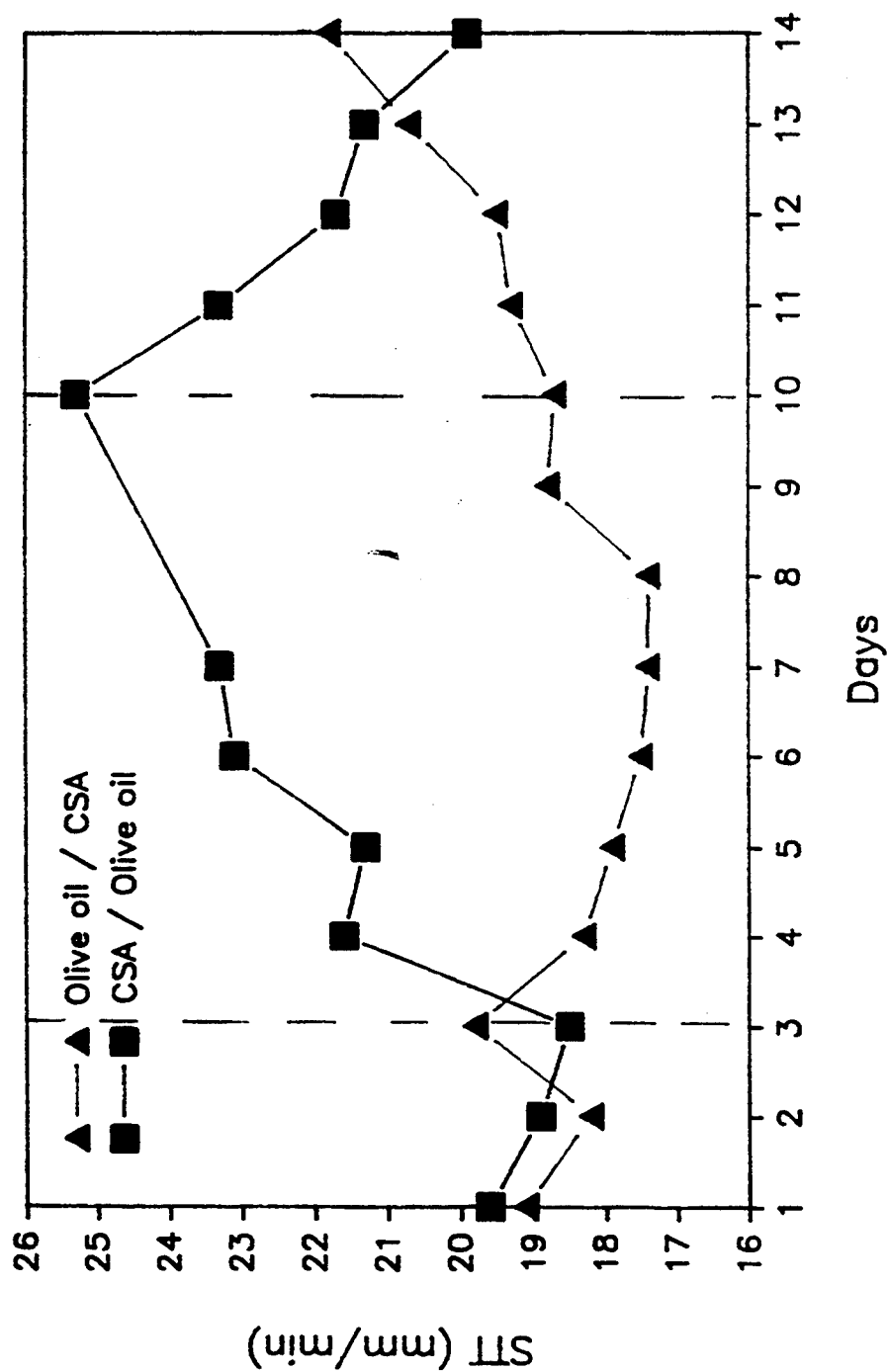

OCULAR CYCLOSPORINE COMPOSITION

This is a continuation of U.S. Ser. No. 07/187,823 filed Apr. 29, 1988, now abandoned, which is a continuation-in-part of U.S. Ser. No. 092,466 entitled "Method of Increasing Tear Production by Topical Administration of Cyclosporin" filed Sep. 3, 1987, now U.S. Pat. No. 4,839,342, issued Jun. 13, 1989 by Renee Kaswan and U.S. Ser. No. 117,218 entitled "Method of Treating a Specific Antigen Mediated Immune Response by Local Administration of Cyclosporin" filed Nov. 4, 1987 by Renee Kaswan, now abandoned.

BACKGROUND OF THE INVENTION

Cyclosporine is a metabolite isolated from the culture broths of the fungal species Tolypocladium inflatum Gams. A neutral, hydrophobic cyclic peptide composed of eleven amino acid residues, cyclosporine includes a previously unknown N-methylated amino acid composed of nine carbon atoms. A number of additional cyclosporines (B, C, D, E, and G) have been reported since the first cyclosporine was isolated (CsA). As described in U.S. Pat. No. 4,117,118 issued Sep. 26, 1978 to Harriet al, cyclosporine is readily soluble in most of the usual organic solvents and practically insoluble in petroleum ether and water. As distributed by Sandoz Ltd, Basel, Switzerland, under the tradename Sandimmune, cyclosporine for oral administration is dissolved in olive oil for further dilution with food and in polyoxyethylated castor oil and ethanol for intravenous injection.

Cyclosporine is a potent immunosuppressive agent used to prolong survival of allogeneic transplants involving skin, heart, kidney, pancreas, bone marrow, small intestine and lung. The exact mechanism of action is not known but experimental evidence suggests that the effectiveness of cyclosporine is due to specific and reversible inhibition of immunocompetent cells, primarily T-helper cells. Lymphokine production, gamma interferon production and release of interleukin-2 or T-cell growth factor are also inhibited by cyclosporine.

Cyclosporine is primarily administered orally or by injection. Unfortunately, parenteral administration of the drug has been associated with renal toxicity, hepatotoxicity, and increased incidence of opportunistic infection. The quantity of drug required for systemic administration is also prohibitively expensive.

As described in U.S. Pat. No. 4,649,047 issued Mar. 10, 1987 to Kaswan, topical administration of cyclosporine is useful in the treatment of a variety of immune mediated disorders of the eye, including uveitis and phacoanaphylactic endophthalmitis. This is also the preferred mode of administration to avoid the undesirable side effects and cost of systemic administration.

As described in U.S. Ser. No. 092,466 now U.S. Pat. No. 4,839,342 (Jun. 13, 1989) entitled "Method of Increasing Tear Production by Topical Administration of Cyclosporin" filed Sep. 3, 1987 by Renee Kaswan, cyclosporine has now been discovered to have additional mechanisms of action which can be used to enhance or restore glandular function, as demonstrated by significant increases in tear production in the eyes of both normal and diseased animals. Although it is not clear at this time how the cyclosporine is achieving this effect, the mechanism of action appears to be independent of the immunosuppressant mechanism.

Although cyclosporine has been topically administered in a variety of vehicles including arachis oil, a commercially available ointment base, and castor oil, the conventional carrier is olive oil. Unfortunately, topical administration of cyclosporine in olive oil to the eye of either humans or dogs is frequently accompanied by a burning sensation, pain, and redness. In some cases, other side effects have been observed including lid edema and periocular alopecia (hair loss around the eye). Similar problems have occurred with topical ophthalmic use of cyclosporine in the other vehicles. Studies have now demonstrated that these unpleasant side effects are due to the carrier, not to the cyclosporine. Unfortunately, cyclosporine is of very limited solubility and the number of acceptable carriers for ophthalmic use is limited.

It is therefore an object of the present invention to provide a composition containing an effective concentration of cyclosporine for topical ophthalmic use which does not cause burning, redness or irritation.

It is a further object of the present invention to provide a composition for topical ophthalmic use which is stable upon storage.

It is another object of the present invention to provide a composition for topical ophthalmic use which promotes normal healing of the epithelial surface of the eye.

SUMMARY OF THE INVENTION

Cyclosporine compositions for topical ophthalmic use for treatment of immune disorders, to enhance or restore tear production, and to enhance or effect normal healing of the surface of the eye, consisting of cyclosporine dissolved in corn oil. The composition may further include antioxidants, lubricants, antibiotics, antifungals, antivirals, pilocarpine, vasoconstrictors, surfactants, wetting agents, anti-inflammatory agents (i.e. corticosteroids), preservatives, mucolytic agents (i.e. bromhexine, acetylcysteine), as well as other compounds.

The preferred composition is 2% cyclosporine, 1 mole % alpha tocopherol and 0.005% methyl paraben in corn oil.

Despite the apparent similarities in chemical structure, studies demonstrate the significant difference in comfort and incidence of side effects between cyclosporine in previously described carriers such as olive oil and cyclosporine in corn oil, both with and without preservative and antioxidant. These studies also establish that topically applied cyclosporine can be used to promote or effect normal healing and prevent or reverse scar formation on the ocular surface.

BRIEF DESCRIPTION OF THE DRAWINGS

FIG. 1 is a graph demonstrating the effect of topical cyclosporine on lacrimation (STT mm/min) over time (days) in twelve normal male beagle dogs; following three days of baseline measurement with no treatment, six dogs were treated with 2% cyclosporin in olive oil. applied topically two times daily, and six dogs were treated with placebo (olive oil) applied topically two times daily. The STT were determined twice daily in the cyclosporin treated dogs ( — ) and in the olive oil treated dogs ( — ). Following 7 days all dogs were crossed over into the opposite treatment groups for an additional three days.

DETAILED DESCRIPTION OF THE INVENTION

Figure 2A:
FIG. 2 is a comparison of the appearance of the eye of a dog suffering from keratoconjunctivitis sicca before (FIG. 2A) and after (FIG. 2B) treatment for four weeks with 2% cyclosporine.

As disclosed in pending applications U.S. Ser. No. 092,466 entitled "Method of Increasing Tear Production by Topical Administration of Cyclosporin" filed Sep. 3, 1987, now U.S. Pat. No. 4,839,342 issued Jun. 13, 1989, by Renee Kaswan, U.S. Ser. No. 117,218 entitled "Method of Treating a Specific Antigen Mediated Immune Response by Local Administration of Cyclosporin" filed Nov. 4, 1987, now abandoned, by Renee Kaswan and U.S. Pat. No. 4,649,047 issued Mar. 10, 1987 to Kaswan, cyclosporine can be topically applied to the surface of the eye to treat both immune mediated eye disease and eye disease of unknown etiology. It can also be used to inhibit corneal graft rejection.

Since cyclosporine has very low solubility in most solutions which can be administered to the eye, the cyclosporine in the majority of studies on tile efficacy of topical administration of cyclosporine has been suspended in olive oil. Unfortunately, controlled studies comparing olive oil alone and in combination with cyclosporine demonstrate that the vehicle, the olive oil, produces redness and burning. In animals, pain is evidenced by the animal holding its eyes shut. In approximately 5 to 10% of approximately 1000 months of treatment (based on number of bottles of 2% cyclosporine dispensed for veterinary use where one bottle is sufficient for treatment of an animal twice daily for about one month), other side effects were observed, including lid edema, corneal surface irregularities, and periocular alopecia.

The present invention is the surprising discovery that corn oil can be substituted for olive oil as the vehicle for topical administration of cyclosporine to the eye to avoid the undesirable side effects due to the use of the olive oil. Over 3000 bottles of 2% cyclosporine have now been dispensed for treatment of animals twice daily without any apparent side effects for periods of time up to four months.

Additives to the corn oil which enhance stability of the cyclosporine solution include antioxidants such as alpha tocopherol and preservatives such as methyl paraben. Other antioxidants are known to those skilled in the art. There are some indications that alpha tocopherol (Vitamin E) may also have beneficial effects on the eye since oxidative radicals increase inflammatory damage. Preliminary clinical observations on the protective action of oral administration of vitamins A and E on the corneal epithelium were recently published by Gerhardinger, et al., in *Acta Vitaminol. Enzymol.* 7(Supp),- 71-74 (1985). Other compounds which may be added to the cyclosporin solution include emollients, viscosity modifying agents, antioxidants, preservatives, antibiotics, antifungals, antivirals, lubricants, surfactants, vasoconstrictors, DMSO, parasympathomimetics, cholinergics, neurotransmitters, lacrimogenic agents, substance P agonists, substance P antagonists, mucolytics, prostaglandin antagonists, lipogenase inhibitors, cyclooxygenase inhibitors, antiinflammatories, oxygen scavengers, hydrating agents, and epitheliotrophic agents. Specific examples, in addition to alpha tocopherol and methyl paraben, include vitamin A, retinoic acid, pilocarpine, hyaluronic acid, polyvinyl alcohol, methylcellulose, eledoisin, physalaemin, bromhexine, mucosolvan, acetylcysteine, indomethacin, and corticosteroids.

The preferred formulation for topical ophthalmic use consists of 2% cyclosporine, 1 mole % alpha tocopherol and 0.005% methyl paraben. However, cyclosporine solutions can be prepared of between approximately 0.01% by weight and saturation, approximately 20% by weight. Unless otherwise specified, all percentages of compounds herein are by weight.

Although the usual means of administration of the compound is by administration of cyclosporin drops to the surface of the eye, delayed or prolonged release of the cyclosporin at a selected site can also be achieved by encapsulating the cyclosporine-oil mixture within a polymeric implant, liposomes, or microcapsules. Methods for making polymeric implants for ocular use are taught by U.S. Pat. No. 3,960,150 to Hussain et al. Both non-degradable and biodegradable polymers can be used, including polyethylene, polystyrene, polypropylene, polyanhydrides, polyorthoester, polylactic acid, and polyglycolic acid. Methods for encapsulating materials within liposomes are taught by PCT/US85/00220 publication WO 85/03640 29 August 1985 by the Liposome Company. Methods for encapsulation of biological material within microcapsules for implantation are taught by U.S. Pat. No. 4,352,883 to Lim. Other suitable methods and materials are known to those skilled in the art.

The following non-limiting examples demonstrate the efficacy of topical cyclosporine in treatment of immune disorders, enhancement or restoration of tear production, and enhancement or effecting of normal healing of the surface of the eye Example 1: Stimulation of tearing in humans suffering from Sjogren's syndrome.

Sjogren's syndrome is characterized by chronic infiltration of the exocrine glands, principally the lacrimal and salivary glands, by mononuclear leukocytes. The process causes the progressive destruction of the glandular tissue and is characterized by the development of keratoconjunctivitis sicca (KCS), or "dry eye". Neither topical nor parenteral treatment using steroids has been completely effective in decreasing irritation of the corneal surface nor in preventing corneal ulcer formation. In fact, topical or parenteral corticosteroids do not enhance lacrimation and can retard healing of corneal ulcers and are therefore considered to be contraindicated by many opthalmologists.

A human patient with primary Sjogren's syndrome (dry eye with dry mouth) was treated with topical 2% cyclosporine in corn oil. The patient had been treated for years with conventional therapy, artificial tears Q 15 mins. For the past several months his STT were 2-3 mm/5 min/eye. (In humans the STT is measured for 5 minutes, unlike the dog where it is measured for only 1 min. However, the expected normal values are the same, i.e., normal is 14 mm, values under 5 mm are indicative of a severe case of dry eye).

Following 9 days of twice daily therapy of both eyes, his STT was 20 and 23 mm/5 min/eye, a significant increase over the pretreatment values. Prior to treatment, the corneas had stained diffusely in both eyes with fluorescein dye, an indication of corneal ulcers. After 9 days of therapy, one eye had no staining and one eye only stained over ⅓ of the surface.

Three women with severe chronic secondary Sjogren's syndrome were treated for 1 week with BID 2% cyclosporine in corn oil containing 1 mole% alpha tocopherol and 0.005%methyl paraben. All three had abnormal corneas. The first had a non-healing corneal ulcer which penetrated the full thickness of the surface epithelium covering the cornea. This ulcer healed within two days of onset of therapy. The second had a "contact lens cornea", an indentation at the circumference of the cornea which gives it the appearance of an eye wearing a contact lens, when no lens is present, which is analogous to a scar. The indentation showed evidence of filling in within 7 days of therapy. The third had corneal lesions which also showed improvement within one week. All had increases in the STT.

The results conclusively demonstrate the effectiveness of topically administered cyclosporine in alleviating the symptoms of KCS, promoting normal healing and actually reducing scar tissue on the surface of the eye.

Example 2: Stimulation of tearing in normal dogs.

Studies were conducted on the effect of applying topical 2% cyclosporine in olive oil to the eyes of normal dogs. The results are shown in FIG. 1 comparing the effect of topical cyclosporine on lacrimination in six normal male beagle dogs, before and after several days of olive oil therapy alone. In both studies, no treatment was given on days 1 to 3 to establish a baseline. On days 4–10, as graphed by the triangles, one drop of olive oil was administered twice daily (BID) to each eye. On days 11–13, one drop of 2% cyclosporine in olive oil was administered twice daily. A significant increase in tearing was observed. On days 4–10, as graphed by the squares, one drop of 2% cyclosporine in olive oil was administered twice daily. On days 11–13, one drop of olive oil was applied to each eye twice daily. The significant increase in tearing observed over days 4–10 persisted through days 11–13 in the absence of cyclosporine treatment.

The data conclusively demonstrate that topically applied cyclosporine increases glandular function, i.e., lacrimination, in normal eyes.

Example 3: Topically applied cyclosporine: Lacrimomimetic effects and reduction of corneal scars in dogs with KCS.

Twenty five cases (23 bilateral, 2 unilateral cases) of spontaneous KCS were treated with a solution of 2% cyclosporine (CsA) in olive oil, 1 gtt QD—BID, OU, and evaluated for changes in tear production as determined by Schirmer tear test (STT) and for changes in the surface of the globe.

The effects of cylosporine were twofold: cyclosporine increased tear production in 84% of idiopathic cases of canine KCS and cyclosporine caused marked regression of corneal pathology including superficial granulation tissue, neovascularization and pigmentation, without retarding healing of corneal ulcers. Case histories are summarized in Table 1.

The diagnosis of KCS preceded CsA use by 0–60 months, with an average of 1.1 yr. Prior treatment included artificial tears in 16/25 dogs, oral or topical pilocarpine in 11/25 dogs, oral or topical corticosteroids in 11/25 dogs, topical antibiotics in 9/25 dogs, or no prior treatment in 5/25 dogs.

Contrary to expectation, the longevity of KCS did not correlate inversely with response to therapy. The average STT before administration of cyclosporine was 2.54 mm/min right eye and 2.46 mm/min left eye. During the period in which cyclosporine eyedrops were administered, the mean STT value was 11.38 mm/min right eye and 11.50 mm/min left eye. The average increase in STT was 8.84 mm/min right eye (t=7.5 Student's T-test for related measures, p<0.0005), and 9.04 mm/min left eye (t=6.7, p<0.0005). 38 eyes were initially diagnosed as having severe KCS (STT 0–4 mm/min). Following treatment, STT values increased by greater than 5 mm/min in 84% of severely affected eyes. Dogs were noted to have increased STT beginning 3 to 56 days after onset of cyclosporine therapy. Of the six eyes (6/38, 16%) determined to be nonresponsive, five were evaluated for only a short period (7 to 35 days). Because STT value in responsive eyes increased with increased frequency and duration of treatment (see Table I, cases 21 and 22), the 84% success rate may be an underestimate.

In six dogs whose STT values increased in response to cyclosporine, treatment was discontinued and the STT values regressed. When cyclosporine was reinstituted, the STT increased back to maximal levels in six hours in one case, and in 1–7 days in the other four cases. In two dogs receiving cyclosporine on alternate days, the STT values decreased on nontreatment days. Even with sporadic interruptions in administration of cyclosporine treatment, no dog has lost responsiveness to cyclosporine. Many of the cyclosporine responsive dogs previously had been unresponsive to corticosteroids administered topically, subconjunctivally, and parenterally.

In dogs with superficial corneal granulation tissue, continuous use of cyclosporine resulted in a progressive decrease in the abnormal thickness and opacity of the cornea. Even in dogs that did not have an increase in tear secretion, alleviation of the corneal disease was generally marked. Most dogs with dense blinding pigmentation and superficial granulation had marked clearing of the corneas after several months of treatment. Three dogs had corneal ulcers at the onset of treatment with cyclosporine; each healed within 48 hours of onset of treatment. Dogs maintained for prolonged periods (8–12 months) relapsed into KCS within 2–3 days of withdrawal of cyclosporine.

TABLE 1

Previous ocular therapy, and Schirmer tear test (STT) values before and while using, cyclosporine eyedrops in 25 cases of canine keratoconjunctivitis sicca.

| Case #, Breed, Sex, Age +/− Keratitis (response to CsA) | Treatment Interval/ Frequency | STT Values Before CsA OD/OS | STT Values With CsA OO/OS |
|---|---|---|---|
| 1. Standard Poodle, F, 7 yr no keratitis | 6 wk/QD | 3/3 | 22/16 |
| 2. Cocker Spaniel, F 7 yr, Pigmentary keratitis (marked improvement) | 5 mo/BID | 0/0 | 10/13 |
| 3. Min. Schnauzer, F/S, 11 yr, Pigmentary keratitis (Marked improvement) | 5 wk/QD | 2/0 | 8/1 |
| 4. Eng. Bulldog, M, 7 yr, Chronic keratitis, visual deficits (Resolved) | 7 wk/BID | 2/3 | 13/20 |
| 5. Samoyed, F/S, 14 yr, Mild keratitis (Resolved) | 1 mo/BID | 2/11 | 18/17 |
| 6. Shih tzy, M, 10 yr Pigmentary keratitis, visual deficits (Marked improvement) | 13 wk/QD | 4/10 | 13/14 |
| 7. Min. Poodle, M, 7 yr, blind dt corneal scarring (Resolved completely) | 16 wk/BID | 0/0 | 11/17 |
| 8. Mixed breed, F/S, 5 yrs diffuse fluorescein uptake (No staining) | 8 mo/BID | 0/0 | 19/17 |
| 9. W H W Terrier, F/S | 4 wks/QD | 0/0 | 13/0 |

TABLE 1-continued

Previous ocular therapy, and Schirmer tear test (STT) values before and while using, cyclosporine eyedrops in 25 cases of canine keratoconjunctivitis sicca.

| Case #, Breed, Sex, Age +/− Keratitis (response to CsA) | Treatment Interval/ Frequency | STT Values Before CsA OD/OS | With CsA OO/OS |
|---|---|---|---|
| 5 yr, Pigmentary keratitis/ blind (Improved visual) | | | |
| 10. Shih tzu M 4 yr, Chronic keratitis O5 (Much improved) | 26 wk/QD | 15/1 | 15/6 |
| 11. Poodle x, F, 6 yr, Mild superficial keratitis (Improved) | 22 wk/QD | 0/0 | 12/18 |
| 12. Shih tzu, F, 3 yr, Pigmentary keratitis (Marked Improvement) | 17 wk/QD | 0/0 | 3/10 |
| 13. Dachsund F, 10 yr, Minimal superficial keratitis (Resolved) | 15 wk/BID | 5/0 | 10/2 |
| 14. Scottish Terrier, M, 12 yr Pigmentary keratitis (50% resolution) | 9 wk/QD | 6/8 | 12/18 |
| 15. Lhasa Apso M/C, 10 yr Pigmentary keratitis (50% resolution) | 8 wk/QD | 13/1 | 18/19 |
| 16. Lhasa Apso M, 9 yr, Pigmentary keratitis (Slight Improvement) | 5 wk/QD | 8/16 | 19/22 |
| 17. Min. Schnauzer, M, 11 yr Pigmentary keratitis/ blind (Slight improvement) | 9 wk/BID | 0/4 | 5/10 |
| 18. Min. Poodle F, 7 yr Marked keratitis (Marked improvement) | 5 wk/QD | 0/0 | 2/1 |
| 19. Cocker Spaniel, F, 1.5 yr no keratitis | 5 wk/QD | 7/5 | 15/10 |
| 20. Boston terrier, F/S, 7 yr, no keratitis | 6 wk/QD | 4/4 | 14/19 |
| 21. Dachsund, M, 3 yr, Mild superficial keratitis (Nearly resolved) | 4 wk/BID | 1/5 | 3/17 |
| 22. Peke/Pomeranian X, F/S 5 yr, Pigmentary keratitis 100% (50% improved) | 12 wk/BID | 0/0 | 20/18 |
| 23. Min. Poodle, M, 9 mo. Chronic keratitis (Marked improvement) | 4 wk/QD | 4/4 | 13/13 |
| 24. Toy Poodle, F/S, 15 yr Chronic keratitis, visual loss (Marked improvement) | 7 wk/BID | 3/0 | 16/0 |
| 25. Peke/Pomeranian, F/S, 6 yr Pigmentary keratitis, blind (Marked improvement/visual) | 11 wk/BID | 0/0 | 8/8 |

Abbreviations:
F (female), M (male), C (castrated), S (spayed)
CsA (2% cyclosporine), QD (once daily), BID (twice daily)
Corneal lesions and changes in the corneal lesions were bilateral unless otherwise indicated.

Example 4: Promotion of normal healing of the eye surface without restoration of normal tearing in a dog.

An 11-year old spayed Miniature Schnauzer had been determined to have KCS 8 months before admission. Analysis of a specimen obtained by conjunctival scraping at that time revealed distemper virus. The dog had been treated with 2% pilocarpine, (1 gtt PO q 12 h) which initially caused an increase in the STT to 8 mm/min bilaterally but later lost efficacy, as the STT decreased to 0 mm/min bilaterally. Treatment had been dexamethasone ointment Q 12 h bilaterally, artificial tears approximately 6 times daily, and petrolatum ointment at bedtime.

Figure 2B:

On admission, ophthalmic observation showed the STT to be 2 mm/min right eye, 0 mm/min left eye, with mucoid conjunctivitis bilaterally, dorsal corneal pigmentation of approximately 40-50% of the corneal surface, and superficial neovascularization extending approximately 6 mm into the dorsal half of the cornea bilaterally (FIG. 2B). The corneal surfaces were modeled irregularly but translucent, and there were no apparent visual deficits. Complete blood count and serum thyroxin were normal and the only abnormality detected on serum profile was an elevated serum alkaline phosphotase (667 mg/dl).

Cyclosporine (2% 1 gtt QD, bilaterally) was prescribed, with artifical tears to be administered as needed. In 4 weeks, the STT had increased to 8 mm/min in the right eye but was still 0-1 mm/min in the left eye. The conjunctivitis had improved, but was still evident in the left eye. However, there was marked improvement of the corneal surface bilaterally (FIG. 2B).

A parotid duct transposition was performed at this time and the lacrimal gland of each third eyelid biopsied. Microscopically both glands were similar, with diffuse often intense periductal and interstitial infiltration of plasma cells and lymphocytes, and fibrosis of the acini and tubules. Focal areas of normal acinar tissue were seen in each gland, and some areas contained dilated tubules lined with flattened epithelium.

The results in Examples 3 and 4 establish that topically applied cyclosporine can be used to resolve corneal ulcers even in the absence of restoration of tearing. As dramatically shown by FIGS. 2A and 2B, the eye surface becomes clearer, smoother, and vision is improved.

Example 5: Comparison of olive oil and corn oil vehicles for cyclosporine for topical ophthalmic use.

Among the animals treated with cyclosporine in olive oil, within four days of beginning treatment, four dogs and one cat had ocular irritation reactions including: hyperemia of the bulbar conjunctiva, corneal surface irregularities with apparent corneal edema, and blepharospasms indicative of ocular pain.

In each case therapy was withdrawn and these symptoms resolved. Therapy with cyclosporine in corn oil was begun in three of the dogs following resolution of the ocular irritation reactions. All three dogs tolerated the corn oil/cyclosporine mixture well.

In the fourth dog, cyclosporine in olive oil was used less frequently than the BID prescription because the owner thought the drug irritated the eyes, but kept using it on an infrequent basis. Following two to three weeks of use, bilateral periocular alopecia occured and the lids were intensely hyperemic. The cyclosporine in olive oil was discontinued for several weeks. Cyclosporine in corn oil was begun BID bilaterally. The lesions of chronic corneal vascularization and superficial keratitis resolved markedly, the STT increased, and there was no recurrence of irritation or alopecia.

Olive oil and corn oil were also compared in normal, human eyes. The olive oil produced a burning sensation lasting 15 to 60 minutes. The corn oil produced a milder sensation lasting only 1 to 2 minutes.

No side effects have been noted from use of the 3000 bottles of 2% cyclosporine in corn oil dispensed for animal use, in comparison with the 5 to 10% incidence of side effects in 1000 bottles of 2% cyclosporine in olive oil dispensed for animal use. The substantial difference in tolerance of the two oils is surprising since the chemical nature of olive oil and corn oil is very similar. Tests of the levels of free fatty acids and pH do not indicate any significant differences which could account for the decreased tolerance for olive oil. Substitution of purified olive oil, Sigma Chemical Co., St. Louis, Mo., or first press olive oil, for the Berio brand olive oil, obtained from the grocery store, which was used initially, does not eliminate the irritation.

Modifications and variations of the present invention, an improved cyclosporine composition for topical ophthalmic use, will be obvious to those skilled in the art from the foregoing detailed description of the invention. Such modifications and variations are intended to come within the scope of the appended claims.

I claim:

1. A topical ophthalmic composition comprising a pharmaceutically effective amount of cyclosporin in corn oil.

2. The composition of claim 1 wherein the concentration of cyclosporine is between about 0.01% and saturation.

3. The composition of claim 1 further comprising a compound selected from the group consisting of vitamin A, vitamin E, retinoic acid, pilocarpine, hyaluronic acid, polyvinyl alcohol, methylcellulose, methyl paraben, eledoisin, physalaemin, bromhexine, mucosolvan, acetylcysteine, indomethacin, and corticosteroids.

4. The composition of claim 1 comprising 2% cyclosporine in corn oil.

5. The composition of claim 4 further comprising a compound selected from the group consisting of alpha tocopherol and methyl paraben.

6. The composition of claim 1 wherein said composition is encapsulated.

7. The composition of claim 6 wherein said composition is encapsulated within a polymeric matrix.

8. The composition of claim 7 wherein said composition is encapsulated within a polymeric matrix formed of a polymer selected from the group consisting of polyethylene, polystyrene, polypropylene, polyanhydrides, polyorthoester, polylactic acid, and polyglycolic acid.

9. The composition of claim 6 wherein said composition is encapsulated within liposomes.

10. The composition of claim 6 wherein said composition is microencapsulated.

11. The composition of claim 1 wherein said cyclosporine is in a concentration which stimulates or restores lacrimal gland activity.

12. The composition of claim 1 wherein said cyclosporine is in a concentration which suppresses an immune disorder of the eye.

* * * * *